United States Patent
Igaki et al.

(10) Patent No.: US 8,617,232 B2
(45) Date of Patent: Dec. 31, 2013

(54) MEDICAL CATHETER APPARATUS

(75) Inventors: Keiji Igaki, Kyoto (JP); Hirokazu Yamada, Kyoto (JP)

(73) Assignee: Kyoto Medical Planning Co., Ltd., Kyoto (JP)

( * ) Notice: Subject to any disclaimer, the term of this patent is extended or adjusted under 35 U.S.C. 154(b) by 101 days.

(21) Appl. No.: 13/497,010

(22) PCT Filed: Sep. 9, 2010

(86) PCT No.: PCT/JP2010/005519
§ 371 (c)(1),
(2), (4) Date: Mar. 22, 2012

(87) PCT Pub. No.: WO2011/036852
PCT Pub. Date: Mar. 31, 2011

(65) Prior Publication Data
US 2012/0185030 A1 Jul. 19, 2012

(30) Foreign Application Priority Data

Sep. 25, 2009 (JP) ................................. 2009-221435

(51) Int. Cl.
*A61F 2/06* (2013.01)
(52) U.S. Cl.
USPC ........................................................ 623/1.11
(58) Field of Classification Search
USPC ............................. 623/1.11, 1.12, 1.23, 2.11;
604/508–510; 606/108, 191, 194, 198, 606/200

See application file for complete search history.

(56) References Cited

U.S. PATENT DOCUMENTS

| 5,389,087 A | 2/1995 | Miraki | |
|---|---|---|---|
| 6,380,457 B1 * | 4/2002 | Yurek et al. | 623/1.11 |

* cited by examiner

*Primary Examiner* — Ryan Severson
*Assistant Examiner* — Katherine M Shi
(74) *Attorney, Agent, or Firm* — K&L Gates LLP

(57) ABSTRACT

Present invention is a medical catheter apparatus used for implanting a vascular stent into a vessel of a living body comprising a catheter (2) provided with a balloon (3), on which a vascular stent (4) is mounted, and a sheath into which the catheter is relatively movably inserted. The catheter is provided at the middle portion with a guide wire leading-out opening (11) for leading out the inserted guide wire (9) toward the side direction of the catheter, the sheath is provided at a middle portion with a guide wire drawing-out opening (13) for drawing the guide wire drawn from the catheter out of the sheath, and a guide wire drawing-out guiding mechanism (14) is provided between the guide wire leading-out opening and the guide wire drawing-out opening for guiding the guide wire led out from the guide wire leading-out opening to the guide wire drawing-out opening. The guide wire drawing-out guiding mechanism has a variable length from the guide wire leading-out opening to the guide wire drawing-out opening which varies in accordance with the relative movement of the sheath with respect to the catheter.

9 Claims, 6 Drawing Sheets

MEDICAL CATHETER APPARATUS

TECHNICAL FIELD

The present invention relates to a medical catheter apparatus useful for implanting a vascular stent into a vessel in a living body.

BACKGROUND ART

Heretofore, when stenosis occurs in a vessel of a living body, such as a coronary artery, percutaneous transluminal angioplasty (PTA) is performed in which the stenosed portion in the vessel is expanded to improve the blood flow using a medical balloon catheter.

The site once stenosed, however, is known to have high possibility of restenosis or acute occlusion due to intimal dissection even after PTA. To prevent such acute occlusion or restenosis, a tubular shaped stent is implanted at the site following PTA. The stent is in a contracted state when introduced into a blood vessel, and subsequently expanded in diameter so as to be deployed at the intended site scaffolding the vessel wall from its inside.

The stent to be implanted in a blood vessel is inserted and transported to the intended site in the vessel by using a catheter having a balloon which can be dilated with expansion medium supplied thereto (balloon catheter). Specifically, the contracted stent is mounted onto the balloon provided at the distal portion of the catheter to be inserted into the blood vessel and transported to the intended site together with the balloon. With the balloon inflation by supplying the expansion medium into it, the stent is expanded in diameter, and consequently deployed at the intended site. The once expanded stent keeps its expanded state even after the balloon is deflated by removal of the expansion medium, thereby scaffolding the implanted site radially to allow fluid path for humor such as blood in the vessel lumen.

Implantation of the stent using the above-mentioned catheter follows the procedure below.

First, a guide wire previously inserted in a catheter is inserted into a blood vessel and advanced to pass through a stenosed portion in the blood vessel. Next, the catheter is inserted into the blood vessel with the guidance of the guide wire to position the balloon on which a stent is mounted to the stenosed portion where the stent is intended to be implant. After the balloon is positioned to the stenosed portion along with the stent, expansion medium is supplied to the balloon by using an indeflator or the like, via an expansion medium supplying channel provided in the catheter, to inflate the balloon so that the stent is expanded in diameter to expand the stenosed portion in the blood vessel. After the inflation of the balloon and the expansion of the stenosed portion in the blood vessel, the expansion medium in the balloon is removed to decompress and contract the balloon. At this time, the stent remaining expanded is disengaged from the contracted balloon and deployed at the stenosed portion in the blood vessel to scaffold the inner wall of the blood vessel. Finally, the catheter is removed from the body and stenting is completed.

Examples of catheters for applying the above-mentioned PTA include an over-the-wire type catheter in which a guide wire insertion lumen is formed throughout its entire length from its distal end to proximal end, and a monorail type catheter in which a guide wire insertion lumen is formed from the distal end to a middle portion of the catheter where a port is opened to draw out the guide wire.

Among these catheters, the over-the-wire type catheters are advantageous due to its operatability in passing through the stenosed site with the guide wire, because the guide wire insertion lumen is formed from the distal end to the proximal end of the catheter.

On the other hand, in the monorail type catheters wherein the guide wire runs through only from its distal end to its middle portion, the length of the guide wire contained in the catheter can be shorter than that of the over-the-wire type catheter. The monorail type catheter, therefore, has an advantage that the catheter can be easily exchanged without using an extension guide wire or an exchanging device to draw out the catheter, if the catheter needs to be removed leaving the guide wire behind in the vessel for insertion of another catheter.

Some procedures require a plurality of stents depending on size of the stenosed portion or the shape of blood vessel. In these cases, the catheter on which a stent is mounted needs to be replaced with another one to deploy another stent. To do this, the catheter has to be exchanged quickly with leaving the guide wire behind in the blood vessel. The monorail catheters to implant a stent allow quicker exchange of catheters and efficient implantation of multiple stents. Examples of this kind of monorail type balloon catheters are disclosed in Patent Document 1 and 2.

When implanting a stent into a blood vessel by using a balloon catheter, the stent mounted on the balloon might be dislocated from a correct mounted position or disengaged from the balloon during insertion. In order to solve this problem, the present inventors have proposed a catheter apparatus to implant a stent in which the stent mounted on a balloon along with the balloon are covered with a proactive sheath and both inserted into a vessel (Patent Document 3).

CITATION LIST

Patent Literature

PTL 1: WO2006/020374
PTL 2: Japanese published patent application 2008-104660
PTL 3: WO2004/103450

SUMMARY OF THE INVENTION

Technical Problem

In the catheter apparatus in which a stent mounted on a balloon is covered with a protective sheath, the sheath covers up the stent mounted on the balloon provided at the end of the catheter and is movable relatively to the catheter, which means the sheath covers up almost entire length of the catheter. This hinders advantage of the monorail type catheters which allows guide wire to be drawn out from their middle portion, because the guide wire drawn out from the catheter is still within the sheath.

A technical object of the present invention is to provide a medical catheter apparatus which allows efficient implantation of a stent into a vessel in a living body while protecting the stent mounted on a balloon provided on a catheter.

Another technical object of the present invention is to provide a medical catheter apparatus which allows quick exchange of catheters and efficient implantation of a plurality of stents in a vessel in a living body.

Solution of Problem

To achieve the above-mentioned technical objects, the present invention provides a medical catheter apparatus having a catheter including a balloon at its proximal end to be inflated with an expansion medium to expand a cylindrical vascular stent attached on it, an expansion medium supplying channel to supply the expansion medium to the balloon extending from its distal end to its proximal end, and a guide wire insertion channel to pass a guide wire extending from its distal end to at least a middle portion, and a sheath into which the catheter is inserted, covering the catheter from its distal end where the balloon attaching the vascular stent is positioned through its proximal end, and moving relative to the catheter at its section between the section where it is covering the balloon attaching the vascular stent and the section where it is supposed to expose the vascular stent attached to the balloon. At the middle part of the catheter, a guide wire leading-out opening where the guide wire being inserted from the distal end of the catheter is led out to run along the outer surface of the catheter is provided. At the middle part of the sheath, a guide wire drawing-out opening where the guide wire being lead out from the catheter is drawn out of the sheath. And a guide wire drawing-out guiding mechanism is provided between the guide wire leading-out opening and the guide wire drawing-out opening to connect the guide wire leading-out opening and the guide wire drawing-out opening and guide the guide wire led out from the guide wire leading-out opening toward the guide wire drawing-out opening. This guide wire drawing-out guiding mechanism moves back and forth in accordance with the relative movement of the sheath and the catheter such that the length from the guide wire leading-out opening to the guide wire drawing-out opening is variable.

The guide wire drawing-out guiding mechanism constituting the present invention comprises a first tubular member, the proximal end of which is connected with the guide wire leading-out opening on the catheter, extending along the outer surface of the catheter toward the guide wire drawing-out opening on the sheath, and a second tubular member, the proximal end of which is connected with the guide wire drawing-out opening on the sheath, extending along the inner surface of the sheath toward the guide wire leading-out opening on the catheter, the first tubular member and the second tubular member being fitted their end slidably to allow move back and forth.

The first tubular member is constituted of a tubular member having an outer diameter which is equal to or smaller than an inner diameter of the second tubular member, the end of the first tubular member being inserted into the second tubular member such that the first tubular member is connected with the second tubular member allowing its back-and-force movement.

The second tubular member has a tubular connecting member at its proximal end to be connected with the sheath. The connecting member is connected with the inner surface of the sheath by joining its proximal end to the periphery of the guide wire drawing-out opening to completely cover the guide wire drawing-out opening.

At least the sheath and the second tubular member may be made of a synthetic resin. The connecting member connecting the second tubular member to the sheath may be made of a synthetic resin whose melting point is lower than that of the second tubular member.

The first tubular member constituting the guide wire drawing-out guiding mechanism may be formed as a tubular member inserted in the second tubular member with their overlapped length $L_2$ is longer than $L_1$ which the balloon is moved from its retracted position in the sheath to its exposing position out of sheath.

A restriction member which restricts the length of sheath move relative to the catheter is preferably provided at the proximal end of the catheter drawn out from the sheath end to restrict the exposing length of the distal end of the catheter attaching the balloon from the distal end of the sheath.

In the medical catheter apparatus in the present invention, a connecting member having a catheter drawing-out port is provided at the proximal end of the catheter. The catheter is drawn out of the sheath via the catheter drawing-out port on the connecting member. And the restriction member which restricts the length of sheath move relative to the catheter is provided at the proximal end of the catheter drawn out from the sheath end. The diameter of the restriction member is larger than the inner diameter of the catheter drawing out port to restrict the exposing length of the distal end of the catheter attaching the balloon from the distal end of the sheath.

In a medical catheter apparatus to implant a vascular stent in a vessel such as a blood vessel of a human being, the guide wire drawing-out opening is preferably located apart from the distal end of the sheath by 15 cm to 45 cm each inclusive In addition, the vascular stent mounted on the balloon provided at the distal portion of the catheter is mounted in a contracted state.

Advantageous Effects of Invention

In the medical catheter apparatus according to the present invention, by providing a guide wire drawing-out guiding mechanism in a sheath covering a catheter, the distal portion of which a balloon to mount the stent is provided, to guide a guide wire led out from a middle portion of the catheter toward the side of the catheter, advantages of monorail catheters to prevent dislocation or disengagement of the stent mounted on the balloon are available while allowing quick exchange of catheters.

By using the catheter apparatus according to the present invention, it is possible to achieve quick exchange of catheters, allowing a plurality of vascular stents to be quickly implanted.

In the catheter apparatus according to the present invention, since the guide wire drawing-out guiding mechanism for connecting the guide wire leading-out opening provided in the catheter with the guide wire drawing-out opening provided in the sheath, the guide wire can be drawn out from the middle portion of the catheter and surely led to the guide wire drawing-out opening in the sheath.

The guide wire drawing-out guiding mechanism moves back and forth in accordance with the relative movement between the sheath and the catheter such that its length from the guide wire leading-out opening to the guide wire drawing-out opening is variable. Even when the relative positions of the sheath and the catheter change, the guide wire can be guided to be surely led to the guide wire drawing-out opening provided in the sheath.

In the catheter apparatus according to the present invention, the guide wire drawing-out guiding mechanism which connects the first tubular member linked to the catheter with the second tubular member linked to the sheath such that guide wire is drawn out from the sheath after passing through the first and second tubular member, even when the catheter and the sheath move relatively. Therefore, the guide wire covered by the catheter is drawn from the middle portion of the catheter and reliably led out from the guide wire drawing-out opening provided in the sheath which covers the catheter.

Since the first tubular member connected with the catheter is joined to the second tubular member connected with the sheath by fitting the first tubular member into the lumen of the second tubular member, there is no protrusion which would impede procession of the guide wire in the passage for the guide wire inserted from the distal end of the catheter and guide wire can be surely led to the sheath direction.

Since the second tubular member is connected to the inner surface of the sheath by completely covering the guide wire drawing-out opening, leakage of liquid such as saline solution injected from the proximal end of the sheath is prevented.

Since the second tubular member is connected to the sheath with the connecting member made of synthetic resin and with lower melting point than that of this tubular member itself, the second tubular member is not subject to thermal effect in joining to the sheath during thermal welding wherein the portion of the connecting member is welded to the inner surface of the sheath.

Since the first and second tubular members constituting the guide wire drawing-out guiding mechanism are overlapped in the length $L_2$ longer than the migration length $L_1$ for the balloon at the distal portion of the catheter which migrates from the distal portion of the sheath to the position where it exposes from the sheath by pulling the sheath with respect to the catheter, disengagement of the first tubular member from the second tubular member can be avoided at any time and the guide wire inserted into the catheter can be surely led out of the sheath.

Since the restriction member is provided at the proximal portion of the catheter for restricting the amount of protrusion of the distal portion of the catheter attaching the balloon out of the distal portion of the sheath, the vascular stent can be safely implanted.

Reliable restriction of the migration of the catheter can be obtained with a simple configuration in which the diameter of the restriction member is larger than the inner diameter of the catheter drawing port.

The cylindrical vascular stent can be surely held by the sheath preventing disengagement or dislocation of the stent from the balloon, because it is mounted on the balloon in a contracted state.

DESCRIPTION OF EMBODIMENTS

The present invention is described hereinafter based on illustrative embodiments of the catheter apparatus used in percutaneous transluminal angioplasty (PTA) to expand the stenosed site in a vessel of a living body, such as a blood vessel, to improve blood flow.

Figure 1:
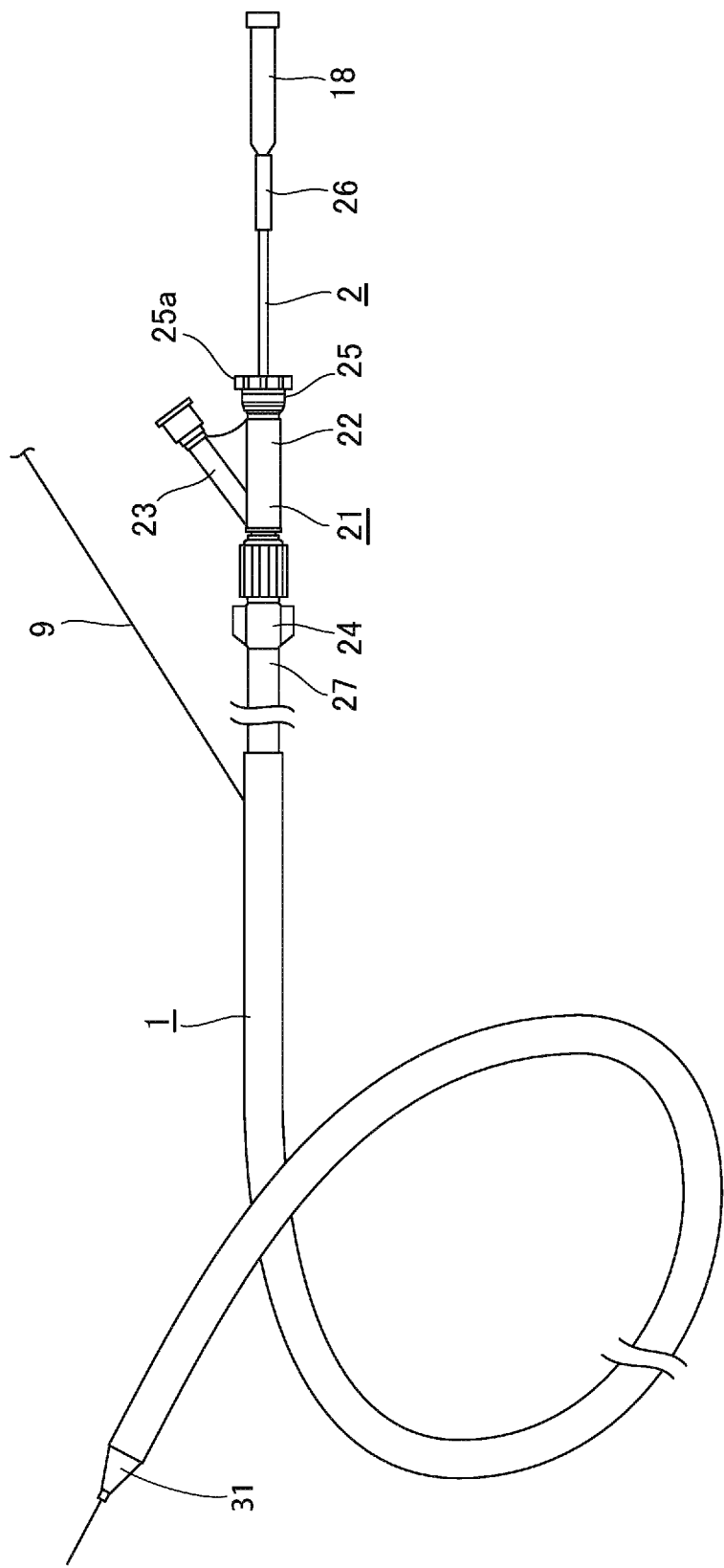
FIG. 1 is a perspective view of a medical catheter apparatus according to the present invention showing its appearance.
Figure 2:
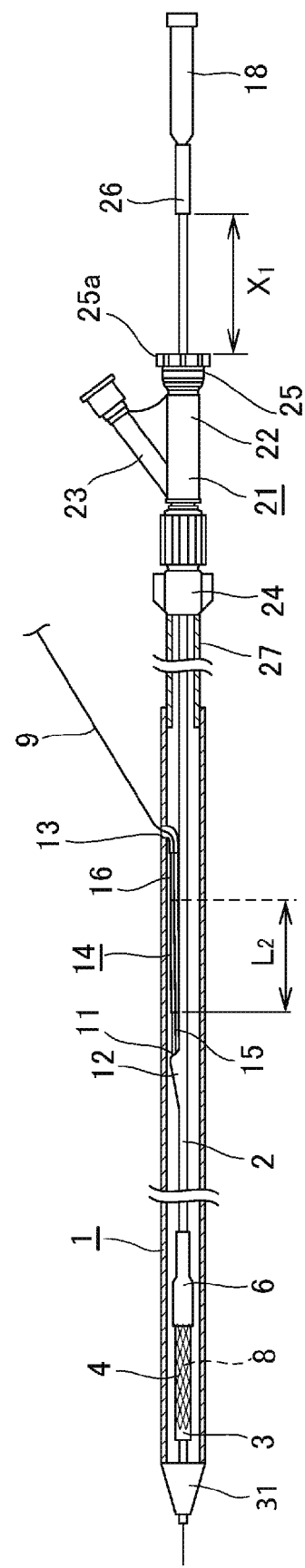
FIG. 2 is a cross-sectional view showing a catheter and a sheath of the catheter apparatus according to the present invention wherein the balloon on the distal portion of the catheter and the stent mounted on the balloon are covered with the sheath.

The catheter apparatus according to the present invention includes a protective sheath 1 and a catheter 2 contained in the sheath 1 with movability to back and forth, as shown in FIGS. 1 and 2.

Figure 3:
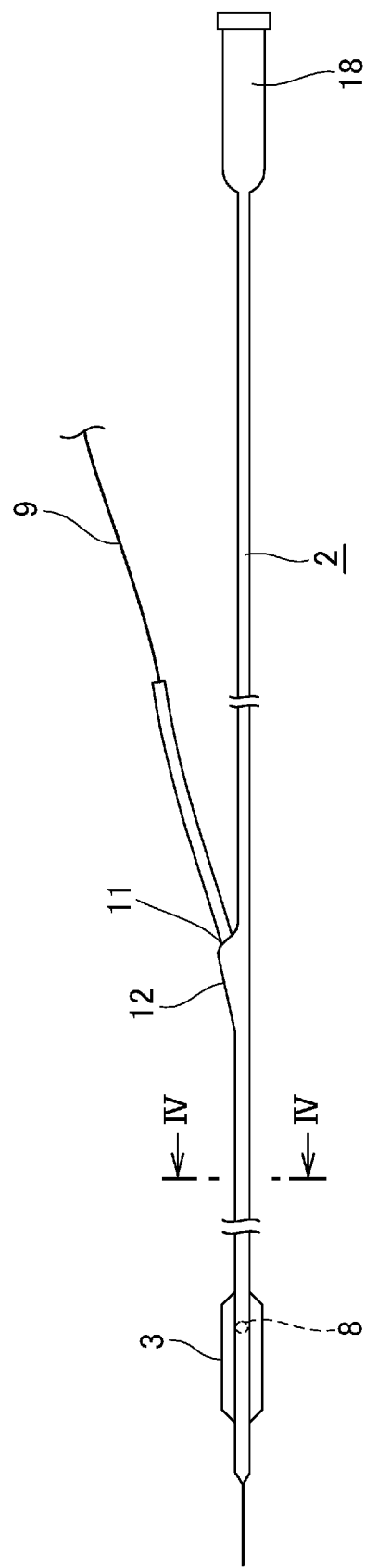
FIG. 3 is a side view of the catheter constituting the catheter apparatus according to the present invention.

The catheter 2 constituting this catheter apparatus is a long tubular body with the diameter of one (1) to two (2) mm and the entire length of 70 to 150 cm as shown in FIG. 3. This catheter 2 is shaped such that it can be deformed in accordance with a curved or tortuous vessel in a living body, such as a blood vessel. Conventional types of vascular catheters may be used as the catheter 2. The sheath 1 is also made of flexible material which deforms in longitudinal direction. In this embodiment, the sheath 1 is made of polyamide resin.

At the distal end of the catheter 2, a balloon 3 which is inflated by an expansion medium such as a contrast medium is provided as shown in FIGS. 2 and 3. On the outer periphery of this balloon 3, a stent 4 to be deployed in the desired site in the blood vessel is mounted. This stent 4 is formed into a cylindrical shape with a channel therein extending from its one end to the other by using, for example, a strand of biodegradable polymer. This cylindrically shaped stent 4 is mounted on the outer periphery of the balloon 3 and will be expanded in diameter along with inflation of the balloon 3.

The proximal side of the stent 4 mounted on the balloon 3 is held by a stent holding member 6. The stent holding member 6 is provided so as to prevent the stent 4 from being displaced relative to the balloon 3 during stent expansion, and to ensure reliable expansion of the stent 4 in accordance with the inflation of the balloon 3.

The catheter 2 is provided with an expansion medium supplying channel 7 through which an expansion medium for expanding the balloon 3 flows. The expansion medium supplying channel 7 is formed as a continuous channel which extends from the proximal end of the catheter 2 to the distal end thereof on which the balloon 3 is provided. As shown in FIG. 3, the catheter 2 on which the balloon 3 is attached has a through hole 8 communicated with the expansion medium supplying channel 7. Via the through hole 8, expansion medium supplied to the expansion medium supplying channel 7 flows into the balloon 2 to fill the balloon 3, or the expansion medium filling the balloon 3 is evacuated.

Figure 4:
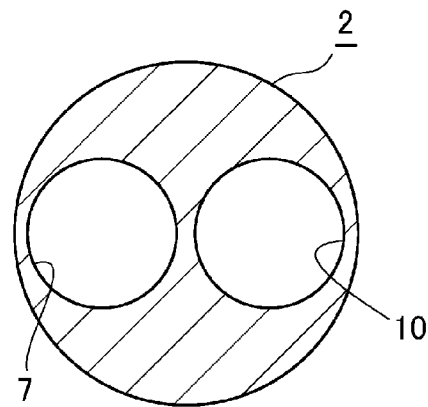
FIG. 4 is a cross-sectional view taken along the line IV-IV in FIG. 3.

The section extending from the distal end to the middle portion of the catheter 2 is provided with a guide wire insertion channel 10 into which a guide wire 9 for guiding the catheter 2 is inserted. Thus, as shown in FIG. 4, the section from the distal end of the catheter 2 to the middle portion of the catheter 2 has two channels, the expansion medium supplying channel 7 and the guide wire insertion channel 10, which are paralleled independently.

The distal open end of the guide wire insertion channel 10 is opened to the distal end of the catheter 2 and its proximal open end opened to the side of the middle portion of the catheter 2. The proximal open end is used for a guide wire leading-out opening 11 for leading the guide wire 9 out of the catheter 2. As shown in FIG. 3, the portion of the catheter 2 where the guide wire leading-out opening 11 is provided is formed as a bulge 12 which gradually bulges toward side direction to make a slope. The guide wire leading-out opening 11 is formed by cutting the proximal side of the bulge 12 obliquely to the longitudinal line of the catheter 2. The cross section of the bulge 12 tilts toward the periphery of the catheter 2 to have large tilt angle to the leading-out direction of the guide wire 9. Consequently, the guide wire 9 can be smoothly led out from the catheter 2.

The guide wire insertion channel 10 is provided within the range of 10 to 40 cm from the distal end of the catheter 2. Thus, the guide wire leading-out opening 11 is provided within 10 to 40 cm from the distal end of the catheter 2.

As shown in FIG. 2, a guide wire drawing-out opening 13 is provided in the middle portion of the sheath 1 containing the catheter 2, which is to draw out the guide wire 9 led out from the guide wire leading-out opening 11.

Between the guide wire leading-out opening 11 opened on the catheter 2 and the guide wire drawing-out opening 13 opened on the sheath 1, a guide wire drawing-out guiding mechanism 14 connecting the guide wire leading-out opening 11 and the guide wire drawing-out opening 13 is provided for guiding the guide wire 9 led out from the guide wire leading-out opening 11 to the guide wire drawing-out opening 13.

The guide wire drawing-out guiding mechanism 14 moves back and forth in accordance with the relative movement of the sheath 1 to the catheter 2, varying the distance between the guide wire leading-out opening 11 and the guide wire drawing-out opening 13. The length of this guide wire drawing-out guiding mechanism 14 varies in accordance with changes of the distance between the guide wire leading-out opening 11 and the guide wire drawing-out opening 13 caused by the relative movement between the sheath 1 and the catheter 2. Therefore the guide wire 9 drew out from the catheter 2 toward the sheath 1 can remain linear without warping or bending.

In this embodiment, as shown in FIG. 2, the guide wire drawing-out guiding mechanism 14 comprises a first tubular member 15, the proximal end of which is connected with the guide wire leading-out opening 11 on the catheter 2, extending along the outer surface of the catheter 2 toward the guide wire drawing-out opening 13 on the sheath 1, and a second tubular member 16, the proximal end of which is connected with the guide wire drawing-out opening 13 on the sheath 1, extending along the inner surface of the sheath 1 toward the guide wire leading-out opening 11 on the catheter 2.

The first and second tubular members 15 and 16 are a hollow tubular member with an inner diameter sufficient to accommodate the guide wire 9. The tubular member 15 and 16 used in this embodiment are preferably formed of a tube made of synthetic resin with smooth and less frictional surface wherein the guide wire 9 formed of a thin metal wire with diameter of 0.3 to 0.6 mm can be smoothly inserted. In this embodiment, the first and second tubular members 15 and 16 are formed of polyimide synthetic resin.

Figure 5:
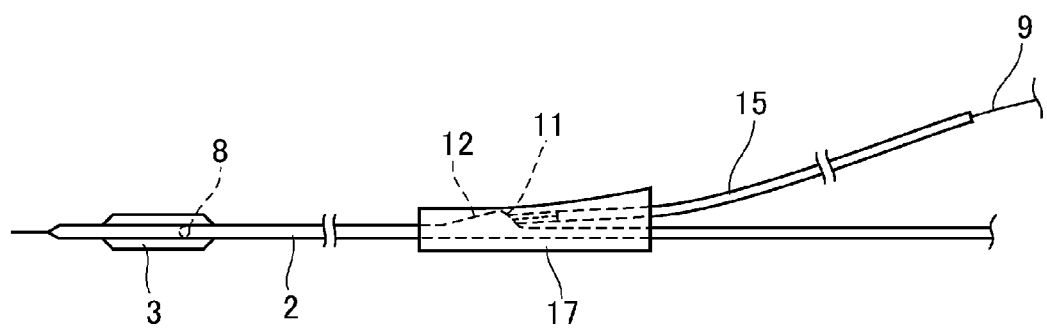
FIG. 5 is a side view of the first tubular member constituting the guide wire drawing-out guiding mechanism connected with the catheter.

As shown in FIG. 5, the first tubular member 15 is connected with the catheter 2 by fitting its one open end to the guide wire leading-out opening 11 and extends along the outer surface of the catheter 2. The proximal end of the first tubular member 15 is clamped to the catheter 2 with a ring-shaped member 17 made of synthetic resin provided on the outer periphery of the catheter 2 to avoid its disengagement from the catheter 2.

The second tubular member 16 is connected with the sheath 1 by joining the surface of its proximal end to the periphery of the guide wire drawing-out opening 13. The distal end of the second tubular member 16 extends along the inner surface of the sheath 1 toward the guide wire leading-out opening 11.

Figure 6:
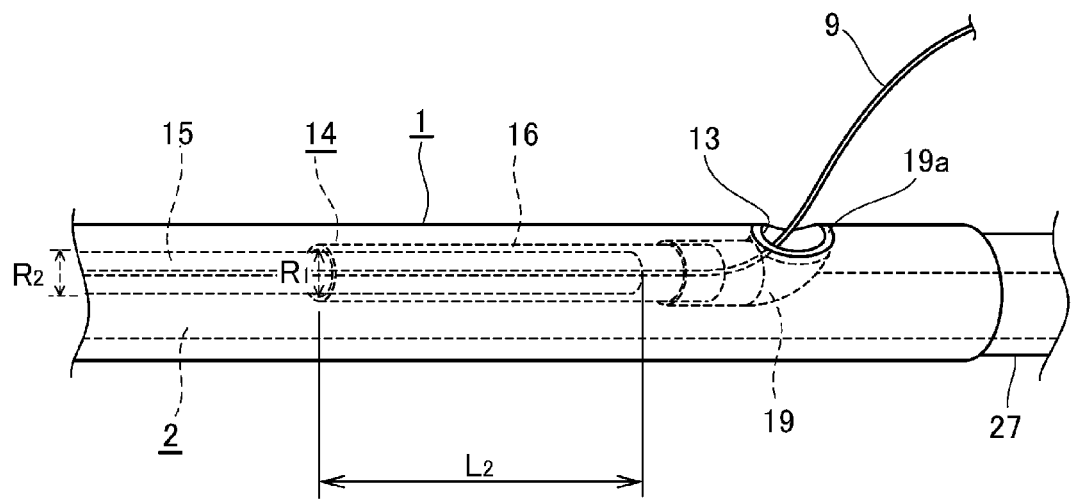
FIG. 6 is a perspective view of the guide wire drawing-out guiding mechanism wherein the balloon on the distal portion of the catheter and the stent mounted on the balloon are covered with the sheath.
Figure 7:
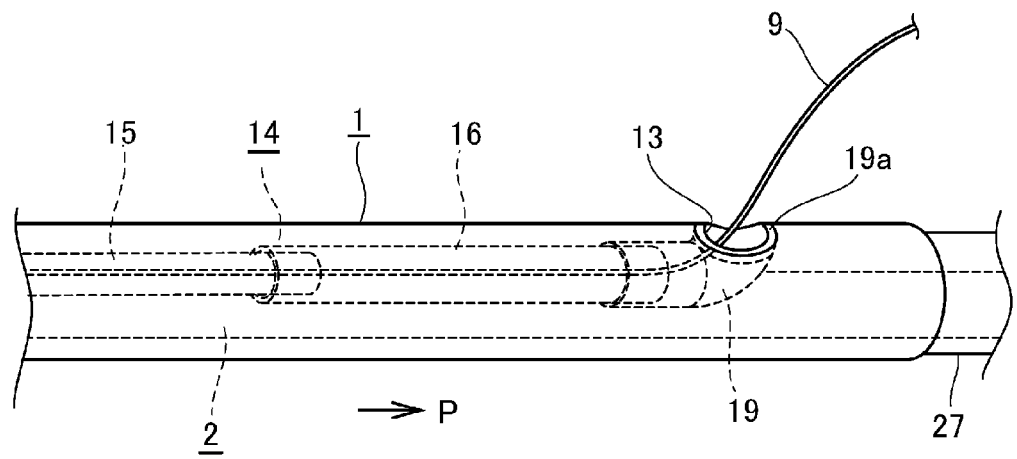
FIG. 7 is a perspective view of the guide wire drawing-out guiding mechanism wherein the balloon on the distal portion of the catheter and the stent mounted on the balloon are exposed from the sheath.

In this embodiment, as shown in FIGS. 6 and 7, the second tubular member 16 is connected with the sheath 1 via a connecting member 19 made of synthetic resin. The connecting member 19 is connected with the second tubular member 16 by fitting its one end to the proximal end of the second tubular member 16. The joint part of the connecting member 19 with the second tubular member 16 may be further bonded with an adhesive.

This connecting member 19 is made of synthetic resin having a melting point lower than that of the second tubular member 16. The connecting member 19 is connected with the inner surface of the sheath 1 with its proximal end surface 19a joined to the periphery of the guide wire drawing-out opening 13. The second tubular member 16 is connected to the sheath 1 by joining the connecting member 19 on its proximal end to the sheath 1.

The connecting member 19 is thermally welded to be connected to the sheath 1. The perimeter of the proximal end surface 19a of the connecting member 19 is joined together with the perimeter of the guide wire drawing-out opening 13 such that the guide wire drawing-out opening 13 is completely covered to prevent leakage of liquid such as saline solution injected into the sheath 1 for complete air removal from the catheter apparatus.

It is preferable that the connecting member 19 is made of the same sort of synthetic resin as the sheath 1, whose melting point is same as that of the sheath 1. In this embodiment, the sheath 1 and the connecting member 19 are formed of polyamide resin such that they are welded at almost the same temperature leading to their tight bond.

In this embodiment, thermal effects, such as deformation of the second tubular member 16 due to heat during thermal welding to join the connecting member 19 with the sheath 1, can be avoided, because the connecting member 19 is made of synthetic resin having a melting point lower than that of the second tubular member 16.

In this embodiment, the melting point of the connecting member 19 is lower than that of the second tubular member 16, because the second tubular member 16 is formed of polyimide resin and the sheath 1 and connecting member 19 are formed of polyamide resin.

As stated above and shown in FIG. 6, the proximal ends of the first tubular member 15 connected with the catheter 2 and the second tubular member 16 connected with the sheath 1 are fitted together allowing their back and forth movement. The first tubular member 15 for leading the guide wire 9 led out from the catheter 2 to the sheath 1 is fitted into the inner lumen of the second tubular member 16. In this way, no protrusion which would impede advancement of the guide wire 9 is produced on the inner lumen of the catheter 2 and the sheath 1 where the guide wire 9 runs through, thus smooth advancement of the guide wire 9 is available.

It is preferable that the first tubular member 15 and the second tubular member 16 are fitted each other without large interspace between them such that they can move smoothly when they are moved back and forth with respect to each other. The first tubular member 15 is, therefore, preferably formed as a tubular member having the outer diameter $R_2$ which is equal to or slightly smaller than the inner diameter $R_1$ of the second tubular member 16, as shown in FIG. 6.

As shown in FIGS. 1, 2 and 3, an indeflation port 18 communicated to the expansion medium supplying channel 7 is provided at the proximal end of the catheter 2 to be inserted into the sheath 1. Although not shown in any figure, an indeflator is connected with this indeflation port 18 to supply expansion medium to inflate the baloon 3. The expansion medium provided from the indeflator enters into the indeflation port 18, runs through the expansion medium supplying channel 7, and flows into the balloon 3 to fill it via the through hole 8 opened at the portion of the catheter 2 where the balloon 3 is provided. The stent 4 mounted on the outer periphery of this balloon 3 is expanded in diameter in accordance with the inflation of the balloon 3.

As stated above and shown in FIG. 2, a connecting member 21 from which the catheter 2 is drawn out is provided at the proximal end of the sheath 1 wherein the catheter 2 attaching the balloon 3 is provided allowing its free back and forth movement. This connecting member 21 is provided with a catheter port 22 to draw out the catheter 2 from the sheath 1 and an indeflation port 23 for supplying liquid such as saline solution to remove air in the sheath 1.

The connecting member 21 is attached to the sheath 1 via a connecting hub 24 attached to the proximal portion of the sheath 1. The proximal portion of the catheter port 22 provided in the connecting member 21 includes a clamp fixing mechanism 25 which provides a fixing mean for fixing the relative movement between the sheath 1 and the catheter 2 drawn out from the proximal end of the sheath 1. In this clamp fixing mechanism 25, the screw body is screwed into/out of the catheter port 22 by turning a screw head 25a, thus clamps the catheter 2 and restrains its relative movement to the sheath 1.

Figure 8:
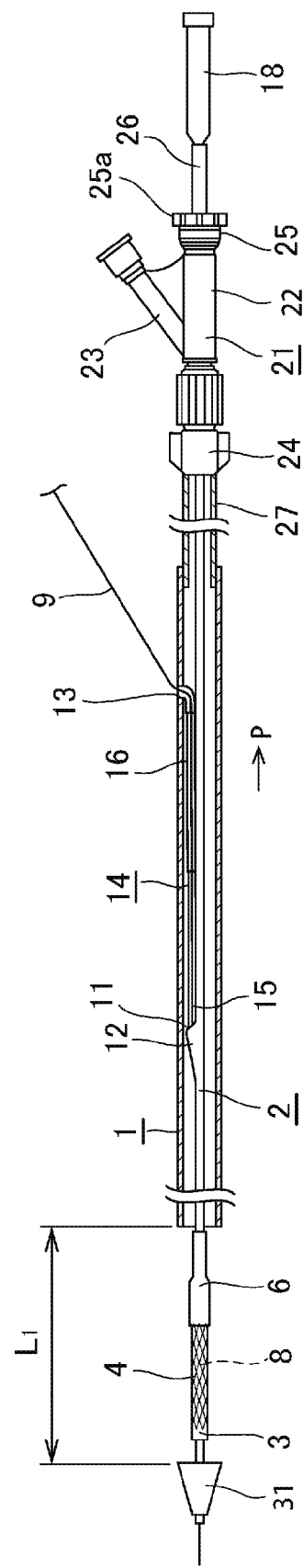
FIG. 8 is a cross-sectional side view showing the stent on the balloon ready to be expanded after exposing the balloon on the distal portion of the catheter along with the stent on this balloon.

In the catheter apparatus according to the present invention, the first tubular member 15 constituting the guide wire drawing-out guiding mechanism 14 is formed as a tubular member having an overlap length $L_2$ longer than an exposing length $L_1$ of the catheter 2 from the sheath 1 at their distal section as shown in FIG. 8, when the sheath 1 is pulled back in the direction of arrow P, that is toward the operator's hand, shown in FIG. 7 with respect to the catheter to inflate the balloon(see also FIGS. 1 and 6). By forming the first tubular member in this way, the connection of the first and second tubular members 15 and 16 can be maintained, even when the sheath 1 is pulled back in the direction of arrow P, that is, toward the operator's body side, with respect to the catheter 2 to uncover the distal portion of the catheter 2 where the balloon is provided. Consequently, even when the distance between the guide wire leading-out opening 11 and the guide wire drawing-out opening 13 is changed according to the pull back of the sheath 1, the connection between the first and second tubular members 15 and 16 is always guaranteed, allowing the guide wire 9 to be surely drawn out toward the side direction of the sheath 1.

As shown in FIGS. 1 and 2, a pullback restriction member 26 is provided at the proximal portion of the catheter 2 drawn out from the proximal portion of the sheath 1 for restricting the pull back distance of the sheath 1 with respect to the catheter 2 to prevent release of the connection between the first and second tubular members 15 and 16. This pullback restriction member 26 is formed as a bulge having a diameter larger than the inner diameter of the catheter port 22 provided in the connecting member 21 attached at the proximal end of the sheath 1. As shown in FIG. 8, the pullback distance of the sheath 1 with respect to the catheter 2 is restricted by the abutment of the open end of the catheter drawing-out port 22 with the distal end of the pullback restriction member 26. Specifically, the pullback restriction member 26 is provided where it can restrict the pullback distance of the sheath 1 with respect to the catheter 2 so as not to lose the overlap between the first and second tubular members 15 and 16, when the sheath 1 is pulled back with respect to the catheter 2 in the shown in FIG. 8 and the second tubular member 16 subsequently moves in the arrow P direction with respect to the first tubular member 1.

The pullback restriction member 26 is provided so that the migration distance $X_1$ of the sheath 1 with respect to the catheter 2 in the direction of arrow P shown in FIG. 8 is shorter than the overlap length $L_2$ of the first and second tubular members 15 and 16.

The stent 4 is reliably expanded by releasing from the balloon 3, because the pullback distance of the sheath 1 with respect to the catheter 2 is restricted at the position where it is pulled back by the length to expose the stent 4 mounted on the balloon 3 outwardly.

In the catheter apparatus according to the present invention, disengagement or dislocation of the stent 4 from the balloon can be surely prevented, because it is reliably mounted in a contracted state on the balloon 3 at the proximal end of the catheter 2.

In addition, in a catheter apparatus according to the present invention, a connection assist member 27, a stiff tubular member, is connected to the proximal portion of the sheath 1. This connection assist member 27 connects a connection hub 24 for the connection of the connecting member 21 with the sheath 1. It is formed of a tubular member made of metal such as stainless steel or aluminum.

Moreover, a stopper 31 is provided at the distal end of the catheter 2 to restrict the retracted position with respect to the sheath 1 of the balloon 3 provided at the distal portion of the catheter 2 and the stent 4 mounted on the balloon. This stopper 31 is tapered and functioning as a guide to help advancement of the catheter 2 in a vessel such as a blood vessel.

An example wherein the stent 4 is implanted in a vessel of a living body such as a coronary artery using a medical catheter apparatus according to the present invention will be explained hereafter.

For implantation of the stent 4 into a blood vessel, a catheter apparatus provided with balloon attaching the stent 4 is prepared. The stent 4 is radially contracted and mounted on the contracted balloon 3 covered by the sheath 1. As shown in FIG. 1, the catheter 2 is contained in the sheath 1 being restricted its relative movement to the sheath 1 by the clamp fixing mechanism 25.

Next, the proximal end of the guide wire 9 advanced toward a stenosed portion in a blood vessel is inserted into the guide wire insertion channel 10 at the distal end of the catheter 2. The guide wire 9 is advanced through the guide wire insertion channel 10, led out from the guide wire leading-out opening 11 provided at the proximal end of the guide wire insertion channel 10 into the first tubular member 15. The guide wire advanced in the first tubular member 15 is led to the second tubular member 16 connected with the first tubular member 15 constituting the guide wire drawing-out guiding mechanism 14. The guide wire 9 led into the second tubular member 16 is drew out through the guide wire drawing-out opening 13 along the sheath 1.

With tightly grasping to secure the end of the guide wire 9 drew out along the sheath 1, the catheter 2 is inserted into the blood vessel with the guidance of the guide wire 9 to deploy the balloon 3 attached on the distal end of the catheter 2 together with the stent mounted on the balloon 3 in the intended site for implantation. The catheter 2 is advanced through the blood vessel together with the sheath 1.

When the balloon 3 reaches the stenosed portion along with the stent 4, fixation of the sheath 1 and the catheter 2 by the clamp fixing mechanism 25 is released and the sheath 1 is pulled back with respect to the catheter 2 in the direction of arrow P shown in FIG. 8 such that the balloon 3 and the stent 4 are exposed from the distal end of the sheath 1. Consequently, the balloon 3 is ready to inflate to expand the stent 4 mounted on the balloon.

When the sheath 1 is pulled back with respect to the catheter 2, the second tubular member 16 moves, along with the sheath 1, in the direction of arrow P shown in FIG. 7 and the second tubular member 16 is pulled from the first tubular member 15. The connection between the first and second tubular members 15 and 16 is maintained, even when the sheath 1 is pulled back with respect to the catheter 2 by the length $L_1$ sufficient for release the support for the balloon 3 at the distal end to expose it from the sheath 1, because the first and second tubular members 15 and 16 are connected with the overlap length $L_2$ longer than the migration length $X_1$ sufficient for release the support for the balloon 3 at the distal end to expose it from the sheath. Consequently, the connection between the first and second tubular members 15 and 16 is maintained such that the guide wire 9 is inserted into them to guide the catheter 2.

The balloon 3 exposed from the distal end of the sheath 1 is inflated, by using the indeflator, with contrast medium supplied through the expansion medium supplying channel 7 in the catheter 2 via the thorough hole 8. When the balloon 3 is inflated, the stent 4 mounted on the balloon 3 is expanded in diameter. The stent 4 thus expanded in diameter comes to be in a state to scaffold the inner wall of the blood vessel from inside. Next, the expansion medium filling the balloon 3 is drawn through the expansion medium supplying channel 7 for decompression and contraction. The stent 4 previously expanded in diameter keeps the expanded state, is disengaged from the balloon 3 contracted in diameter and is remained at the stenting position in the blood vessel such that the implantation for keeping the state scaffolding the inner wall of the blood vessel is accomplished.

After implanting the stent 4 into the implantation site as explained above, the catheter 2 and the sheath 1 are pulled out of the blood vessel with the guidance of the guide wire 9. At this time, since the guide wire 9 is led out toward the side direction from the middle portion of the sheath 1 covering the catheter 2, removal operation can be quickly conducted without using an extensional guide wire. In other words, the catheter apparatus according to the present invention can achieve advantages of monorail catheters, while including the sheath 1 holding the stent 4 mounted on the balloon 3 provided on the catheter 2.

It should be noted that, there are cases where a plurality of stents are implanted in a stenosed portion of the blood vessel. In these cases, since the present invention can implant the stents 4 with quicker exchange of the catheters, which is an inherent advantage of the monorail catheter, the operation can be conducted quickly, thus reducing burden of patients.

As explained hereinabove, the catheter apparatus according to the present invention effectively utilizes the advantages of the monorail catheter, surely prevents dislocation or disengagement of the stent 4 mounted on the balloon 3 provided on the catheter 2, as well as quickly implants the stent 4 in a vessel in a living body, such as a blood vessel.

It should be noted that, the vascular stent 4 mounted on the catheter apparatus according to the present invention is not limited to the illustrative stent made of a biodegradable polymer. Any type of stents including metal stents may be broadly used for balloon expandable stents.

Furthermore, the present invention can be applied to implantations of stents in a vessel of a living body such as an ureter and a bile duct rather than a blood vessel.

EXPLANATION OF REFERENCES

1 sheath
2 catheter
3 balloon
4 stent
7 expansion medium supplying channel
9 guide wire
10 guide wire insertion channel
11 guide wire leading-out opening
13 guide wire drawing-out opening
14 guide wire drawing-out guiding mechanism
15 first tubular member
16 second tubular member
19 connecting member

What is claimed is:

1. A medical catheter apparatus comprising:

a catheter including an outer periphery on which a cylindrical vascular stent is configured to be mounted and a distal portion comprising a balloon which is to be inflated with a supply of an expansion medium to expand the stent in diameter, being provided with at least an expansion medium supplying channel extending from the distal portion to a proximal portion for supplying the expansion medium to expand the balloon, and a guide wire insertion channel extending from the distal portion to a middle portion for inserting a guide wire, and a sheath into which the catheter is inserted, covering the outer peripherly of the catheter from a distal side of the catheter where the balloon attaching the vascular stent is positioned through a proximal side of the catheter, and moving relative to the catheter between the section where the sheath is covering the balloon attaching the vascular stent and the section where the sheath is supposed to expose the vascular stent attached to the balloon, wherein the catheter is provided at its middle portion with a guide wire leading-out opening for leading out the guide wire inserted from the distal portion of the catheter toward a side direction of the catheter, the sheath is provided at its middle portion with a guide wire drawing-out opening for drawing the guide wire drawn from the catheter out of the sheath, a guide wire drawing-out guiding mechanism comprising:

a first tubular member, having a proximal end of which is connected with the guide wire leading-out opening formed on the catheter, extending along the outer surface of the catheter toward the guide wire drawing-out opening formed on the sheath, and a second tubular member, having a proximal end of which is connected with the guide wire drawing-out opening formed on the sheath, extending along the inner surface of the sheath toward the guide wire leading-out opening formed on the catheter, the first tubular member and the second tubular member being connected movably back and forth by slidably fitting their end sections together, wherein the guide wire drawing-out mechanism is provided between the guide wire leading-out opening and the guide wire drawing-out opening for connecting the guide wire leading-out opening and the guide wire drawing-out opening, and for guiding the guide wire led out from the guide wire leading-out opening to the guide wire drawing-out opening, and wherein the guide wire drawing-out guiding mechanism has a variable length from the guide wire leading-out opening to the guide wire drawing-out opening which varies in accordance with the relative movement of the sheath with respect to the catheter.

2. The medical catheter apparatus according to claim 1, wherein the first tubular member is constituted of a tubular member having an outer diameter which is equal to or smaller than an inner diameter of the second tubular member, the proximal end of the first tubular member being inserted into the second tubular member such that the first tubular member is connected with the second tubular member movably back and forth.

3. The medical catheter apparatus according to claim 1, further comprising a tubular connecting member connected to a proximal portion of the second tubular member to be connected with the sheath, wherein the second tubular member is connected with the inner surface of the sheath by joining a proximal end surface of the connecting member to the periphery of the guide wire drawing-out opening and sealing the guide wire drawing-out opening.

4. The medical catheter apparatus according to claim 3, wherein at least the sheath and the second tubular member are made of a synthetic resin material and the connecting member connecting the second tubular member to the sheath is made of a synthetic resin material having a melting point lower than that of the second tubular member.

5. The medical catheter apparatus according to claim 1, wherein the first tubular member constituting the guide wire drawing-out guiding mechanism is formed as a tubular member having a length inserted into the second tubular member with an overlap length $L_2$ which is longer than a migration length $L_1$ by which the balloon provided at the distal portion of the catheter migrates from a distal portion of the sheath to a position which exposes the balloon outwardly when the sheath is pulled with respect to the catheter.

6. The medical catheter apparatus according to claim 5, further comprising a restriction member provided at the proximal portion of the catheter drawn out from a proximal portion of the sheath for restricting an amount of movement of the sheath with respect to the catheter to restrict a length by which the distal portion of the catheter provided with the balloon is exposed out of the distal end of the sheath.

7. The medical catheter apparatus according to claim 5, further comprising a connecting member connected to a proximal portion of the sheath and including a catheter drawing-out port, wherein the catheter is drawn out through the catheter drawing-out port out of the sheath, and further comprising a restriction member provided at the proximal portion of the catheter drawn out through the catheter drawing-out port for restricting an amount of movement of the sheath with respect to the catheter, the restriction member having a diameter larger than the inner diameter of the catheter drawing-out port to restrict a length by which the distal portion of the catheter having provided with the balloon is exposed out of the distal end of the sheath.

8. The medical catheter apparatus according to claim 1, wherein the guide wire drawing-out opening is located apart from the distal end of the sheath by 15 cm to 45 cm each inclusive.

9. The medical catheter apparatus according to claim 1, wherein the vascular stent is configured to be mounted on the balloon provided at the distal portion of the catheter in contracted state.

* * * * *